United States Patent [19]

Baker et al.

[11] Patent Number: 4,847,373

[45] Date of Patent: Jul. 11, 1989

[54] PRODUCTION OF 3-ALLYL- AND 3-BUTENYL-3-CEPHEMS

[75] Inventors: Stephen R. Baker, Cicero; Vittorio Farina, Syracuse; Chester Sapino, Jr., East Syracuse, all of N.Y.

[73] Assignee: Bristol-Myers Company, New York, N.Y.

[21] Appl. No.: 19,395

[22] Filed: Feb. 26, 1987

[51] Int. Cl.$^4$ ............................................. C07D 501/04
[52] U.S. Cl. ..................................... 540/215; 540/222; 540/230
[58] Field of Search ................ 540/215, 222, 225, 230

[56] References Cited

U.S. PATENT DOCUMENTS 4,727,070 2/1988 Kaplan et al. ....................... 540/222

Primary Examiner—Nicholas S. Rizzo
Attorney, Agent, or Firm—Robert E. Carnahan

[57] ABSTRACT

There is disclosed a process for the production of certain 2-allyl- and 3-butenyl-3-cephem derivatives by coupling a 3-chloromethyl-3-cephem with a hydrocarbyltributystannane in the presence of bis(dibenzylideneacetonyl)-palladium and a phosphine. The 3-allyl- and 3-butenyl-3-cephem derivatives so-produced are useful as broad-spectrum antibacterial agents.

7 Claims, No Drawings

PRODUCTION OF 3-ALLYL- AND 3-BUTENYL-3-CEPHEMS

BACKGROUND OF THE INVENTION

1. Field of the Invention

The present invention relates to a process for the production of one of the group of 3-allyl- and 3-butenyl-3-cephems and 3-carbocyclic- and -heterocyclic methyl-3-cephem derivatives by providing a 3-chloroethyl-3-cephem intermediate, reacting the intermediate with an appropriate hydrocarbyl tributylstannane in the presence of bis(dibenzylideneacetonyl)-palladium and a phosphine and a metal halide. The resulting 3-allyl- and butenyl- and -carbocyclic methyl- and -heterocyclic methyl-3-cephems are useful as broad spectrum antibacterial agents.

2. Background Art

Hoshi et al., U.S. Pat. Nos. 4,591,641 (5/86) and 4,520,022 (5/85), both of which are owned by the assignee of the present invention, disclose vinyl-substituted cephalosporins having the 3-((Z)-1-propenyl) and 7-phenylglycylamido groups represented by the structural formula, A,

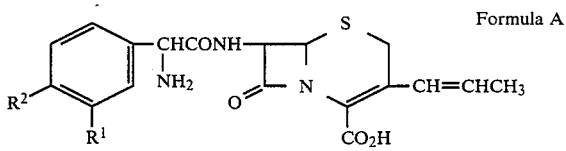

Formula A wherein the 3-propenyl group has the (Z)-configuration. These patented compounds were produced by forming a substituted vinyl group in the 3-position of the cephalosporin nucleus by reacting a 3-halomethyl cephalosporin or an alkyl halide (e.g., methyl halide) with a triarylphosphine to yield a phosphoranyl intermediate which is then treated with a alkylhydrogencarbonyl reagent or a 3-hydrogencarbonyl cephalosporin, respectively. The foregoing compounds were produced by application of the synthetic routes disclosed in U.S. Pat. Nos. 3,769,277 (10/73), 3,994,884 (11/76), and 4,107,431 (8/78).

Long et al., U.S. Pat. No. 3,769,277 (10/73) disclose $\Delta^3$-4-carboxy cephalosporins of the formula

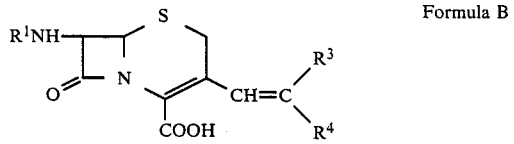

Formula B by reacting a 3-formyl (i.e. a 3-hydrogencarbonyl)cephalosporin with a phosphorane of the formula $R_3P=CR^3R^4$.

Weir, U.S Pat. No. 3,994,884 (11/76) discloses the preparation of $\Delta^3$-4-carboxy cephalosporin having a 3-vinyl group by reacting the corresponding 3-halomethyl cephalosporin compound with a phosphine to obtain the phosphonium intermediate, converting the phosphonium intermediate to the corresponding phosphoranylidene intermediate, and coupling the phosphoranylidene intermediate with formaldehyde.

Clark, et al., U.S. Pat. No. 4,107,431 (8/78) (GB1342241), disclose the preparation of $\Delta^3$-vinyl or substituted vinyl-4-carboxy cephalosporins by reacting a 3-phosphoranylidene cephalosporin with a carbonyl compound of the formula $R^3COR^4$ or by reacting a 3-formyl cephalosporin with a phosphorane of the formula $R_3P=CR^3R^4$.

O'Callaghan et al., U.S. Pat. No. 3,830,700 (8/74), disclose certain 3-arylvinyl cephalosporins useful as chromogenic agents for the detection of $\beta$-lactamase activity. The compounds useful in the patented method were prepared by reacting a 3-phosphoranylidene cephalosporin with a hydrogencarbonyl aryl (aryl aldehyde) compound or by reacting a 3-hydrogencarbonyl cephalosporin with a phosphorane of the formula $(R)_3P=CHAr$.

Beeby, U.S. Pat. Nos. 3,983,113 (9/76), 4,049,806 (9/77), and 4,139,618 (2/79) disclose 3-(heterocyclothio)propenyl cephalosporins represented by the formula

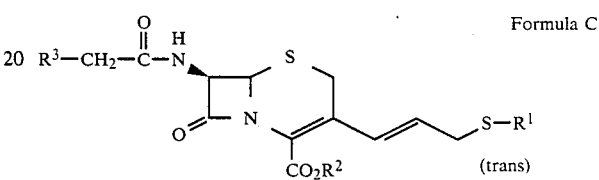

Formula C wherein the compounds were prepared by reacting the starting 3-formyl cephalosporin with a suitable vinyl Grignard reagent to obtain a mixture of $\alpha$- and $\beta$-hydroxy isomers of the corresponding 3-(1-hydroxyprop-2-enyl) cephalosporin followed by treating the foregoing intermediate with a mercapto substituted heterocycle corresponding to the $SR^1$ substituent in the presence of a small amount of strong acid. Beeby, U.S. Pat. No. 4,112,087 (9/78) discloses compound having the formula shown above except that "OR" is substituted for "S—$R^1$".

Webber, U.S Pat. No. 4,065,620 (12/77) discloses 3-(substituted) vinyl cephalosporins prepared by reacting a 3-formyl cephalosporin compound with a phosphorane of the formula $R_1R_2R_3P=CH-Y$ under conventional Wittig reaction conditions.

Takaya et al., EP App. Publn. No. 0,030,630 (6/81) disclose 7-acylamino-3-vinylcephalosporanic acid derivatives prepared by reacting a 3-formyl cephalosporin compound with a suitable phosphorane Miyadera et al., U.S. Pat. No. 4,147,863 (4/79) disclose cephalosporin derivatives having a (1-alkyl-1H-tetrazol-5-yl)vinyl group at the 3-position of the cephem nucleus. The patent discloses preparation of the intermediate having the given 3-vinyl substituent by reacting a known 3-formyl cephalosporin with a Wittig reagent (phosphorane).

Beattie et al., U.S. Pat. No. 4,255,423 (3/81) disclose cephalosporin compounds having a substituted or unsubstituted vinyl group at the 3-position of the cephalosporin nucleus prepared by the reaction of a phosphoranylidene compound with a compound containing a carbonyl group. More particularly, a phosphoranylidene compound of the formula

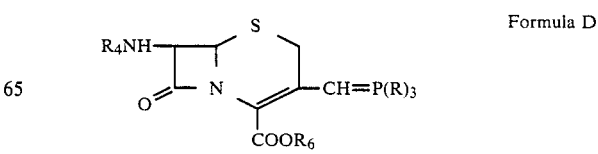

Formula D may be reacted with a carbonyl compound of the formula $R_2-CO-R_3$ to obtain the $-CH=CR_2R_3$ substituent at the 3-position of the cephem nucelus.

It is known in the art to which this invention and the compounds thereby produced relate that it is possible to chemically modify naturally occurring cephalosporins by performing chemical reactions at the C(3)-position and C(3)-position side chain of the 3-cephem nucleus in an effort to discover novel antibiotics. See "Chemistry and Biology of β-Lactam Antibiotics. Volume 1. Penicillins and Cephalosporins," R. B. Morin and M. Gorman, Ed., Academic Press, New York, 1982.

Notaby absent in the field of cephalosporin chemistry is a general method for producing 3-cephem derivatives by means of carbon-carbon bond formation at the C(3')-position of the 3-cephem nucleus.

Heck, R. F. in "Palladium Reagents In organic Synthesis," Academic Press, Orlando, FL, 1985, discloses the use of various Pd reagents in various synthetic operations.

Scott, Crisp and Stille, *J. Amer. Chem. Soc.*, 106, 4630(1984) described the palladium-catalyzed coupling of organotins with electrophiles facilitated by the addition of zinc chloride.

Scott and Stille, *J. Amer. Chem. Soc.*, 108, 3033(1986) described the palladium-catalyzed coupling reaction of several vinyl triflates with organostannanes such as, for example, vinyltributylstannane to yield a product having the vinyl group bonded to the carbon atom which has been vacated by the triflate group.

In connection with work on the development of new broad spectrum semisynthetic cephem antibiotics, we conceived that natural cephalosporins, bearing a potential leaving group at an allylic position, should in principle be amenable to palladium (0)-promoted displacement. Our initial attempts to couple the compound having formula E with vinyltributyl stannance in the presence of Pd catalysts were, however, unsuccessful.

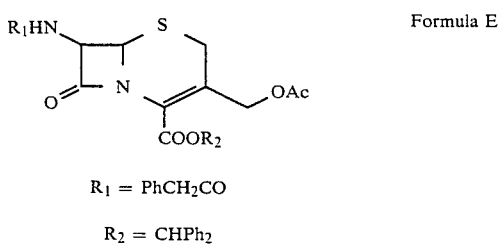

$R_1 = PhCH_2CO$ $R_2 = CHPh_2$

We found that the readily available chloromethyl-cephems (e.g., Otsuka Co.) reacted, albeit extremely slowly, with organostannanes in reluxing THF in the presence of Pd(OAc)$_2$ under conditions reported by F. K. Sheffy, J. P. Goldshalx, and J. K. Stille, *J. Amer. Chem. Soc.*, 106, 4833 (1984). The use of more polar or higher-boiling solvents produced extensive decomposition.

However, using a catalytic system prepared by adding tri-(2-furyl)-phosphine to a THF solution of bis(-dibenzylideneacetonyl)palladium(0), the reaction proceeded at a convenient rate, and coupling with a variety of stannanes (Eq. 1) took place in good yield.

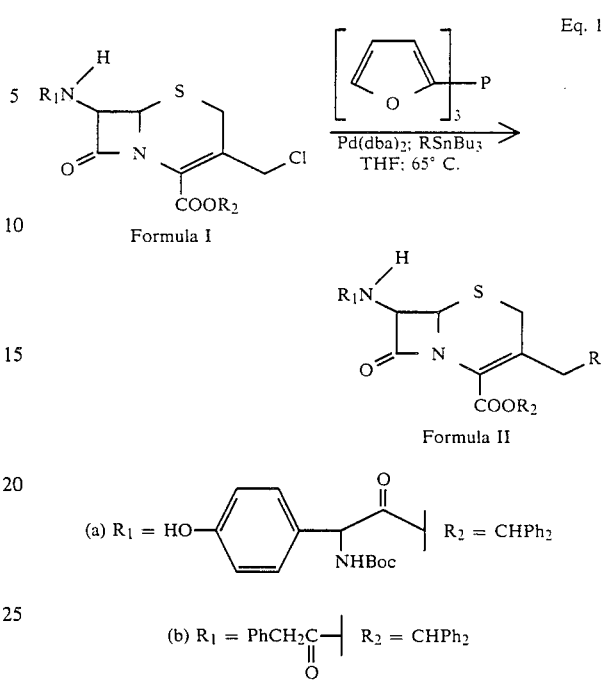

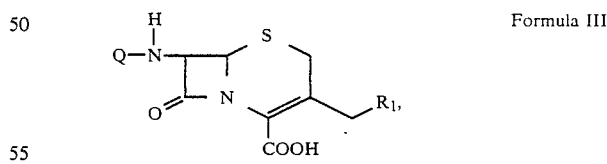

SUMMARY OF THE INVENTION

It has been discovered that coupling between 3-chloromethyl-3-cephems and certain hydrocarbyltrialkyl stannanes can be induced to form a carbon-carbon bond at the 3'-position of the cephem nucleus in satisfactory yield. This is accomplished by carrying out the coupling reaction at reflux in the presence of a relatively polar aprotic solvent, a Pd° or a Pd$^{II}$ compound, and a phosphine reagent, most preferably tri-(2-furyl)-phosphine.

DETAILED DESCRIPTION OF THE INVENTION

This invention is a process for the production of one of the groups of 3-allyl- and 3-butenyl-3-cephems and 3-carbocyclic aryl-methyl- and 3-heterocyclic aryl-methyl-3-cephem derivatives represented by the formula wherein $R^1$ represents a hydrocarbyl group selected from unsubstituted and substituted vinyl(ethylenyl), allyl (propen-3-yl) and carbocyclic and heterocyclic aryl groups and wherein Q represents a group selected from H; an acyl group, R—CO—, wherein R is an organic group having 1–20 carbon atoms and is selected from (a) unsubstituted and substituted carbocyclic and heterocyclic aryl, (b) unsubstituted and substituted, straight-chain and branched-chain, alkyl, (c) unsubstituted and substituted carboxyclic and heterocyclic aralkyl, (d) unsubstituted and substituted carbocyclic and heterocyclic cycloalkyl, (e) unsubstituted and substituted alkenyl, (f) unsubstituted and substituted cycloalkenyl, and (g) unsubstituted and substituted alkynyl; an unsubstituted and substituted trialkylsilyloxycarbonyl and triarylsilyloxycarbonyl; and trialkysilyl and triarylsilyl groups; wherein, when substituted, the alkyl, cycloalkyl, alkenyl, cycloalkenyl and alkynyl group may be substituted with 1 to 3 substituents selected from halo, hydroxy, alkoxy, amino, mono- and dialkylamino, nitro, carboxyl, alkoxycarbonyl, oxmino, and cyano groups and the aryl group may be substituted with 1 to 3 alkyl, hydroxy, alkoxy, halo, amino, mono- and dialkylamino, nitro, carboxyl, alkoxycarbonyl, and cyano groups and pharmaceutically acceptable acid addition and base salts and esters thereof, comprising the steps of:

(A) providing a 3-chloromethyl-3-cephem starting compound in a relatively polar aprotic solvent;

(B) contacting the starting compound from step (a) above with at least an equimolar amount of a hydrocarbyltrialkyl stannane selected from the group of unsubstituted and substituted vinyl-, allyl-, and carbocyclic aryl and heterocyclic aryl trialkylstannanes in the presence of about 1–10 mole % of a palladium compound and about 3–30 mole % of a phosphine reagent under conditions effective to induce chemical reactivity; and (C) recovering the 3-hydrocarbyl-3-cephem product from the reaction mixture from step (B).

By way of example but without limitation, Q in the above formula III may be unsubstituted or substituted hydrocarbyl such as phenacyl ($\phi$CO); phenacetyl ($\phi$CH$_2$CO); t-butyloxycarbonyl(t-BuCO); a group represented by the formula

wherein G is 2- or 3-thienyl or unsubstituted and substituted phenyl and G' is hydroxy, formyloxy, acetoxy, carboxy, sulfo, or amino and substituted amino; a group represented by the formula

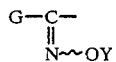

wherein G has the meaning given above and Y is H, methyl or acetyl; a group represented by the formula G—(Z)$_m$—CH$_2$— wherein G has the meaning given above, M is 0 (zero) or 1, and Z is O (oxygen) or S (sulfur); a group represented by the formula

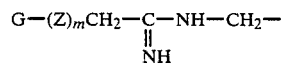

wherein G, Z and m have the meanings given above; and

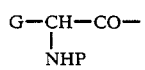

wherein G has the meaning given above and P is anyone of well known protecting groups conventionally used in cephalosporin chemistry with amino, hydroxy and carboxyl groups such as, for example, benzyl, dipheylmethyl, and the like.

The starting 3-chloromethyl-3-cephem can be readily obtained according to well known procedures such as, for example, starting from the known 3-hydroxymethylcephems. The starting 3-chloromethyl-3-cephem may bear various substituents of the 3-cephem nucleus as are known to those skilled in the art to which this invention pertains. The carboxyl group at the 4-position may be in the form of an ester or salt derivative thereof. The 7-position of the 3-cephem nucleus may bear an unsubstituted or substituted amino group wherein the substituent may be selected from any substituent known and reported in the literature. By way of example but without limitation, the 4-carboxyl group may be present as the diphenylmethyl carboxylate ester and the 7-position substituent may be the phenylacetamido or t-butyloxycarbonylamino group.

The aprotic solvent used in the process of this invention should be relatively polar. Thus, the solvent may be selected from 1methyl-2-pyrrolidinone (N-methylpyrolidone), tetrahydrofuran (THF), nitriles such as acetonitrile, dimethylsulfoxide (DMSO), dimethylformamide (DMF), ethers such as glyme and dioxane, hexamethylphosphoric amide (HMPA), acetone, nitromethane and nitrobenzene. Preferably, the solvent is selected from 1-methyl-2-pyrrolidinone, THF, acetonitrile, and DMF. More prefereably, the solvent is selected from N-methylpyrrolidinone, THF and acetonitrile. Most preferably, the solvent is selected from THF and 1-methyl-2-pyrrolidinone.

By the expression "hydrocarbyl" with reference to the 3-hydrocarbyl substitutent on the cephem nucleus derived from the hydrocarbyltrialkylstannane is meant unsubstituted and substituted vinyl (ethenyl), allyl (propen-3-yl) and carbocyclic and heterocyclic aryl trialkylstannanes. When substituted, the vinyl, allyl and carbocyclic and heterocyclic aryl groups may be substituted with 1 to 3 substituents selected from alkyl, halo, hydroxy, alkoxy, amino, mono- and dialkylamino, nitro, carboxyl, alkoxycarbonyl, and cyano groups. Preferred among alkyl substituents are lower (C$_1$ to C$_4$) alkyl and most preferably methyl (CH$_3$). Preferred among alkoxy substituents are lower alkoxy and most preferably methoxy and ethoxy. The halo substituent(s) may be selected from F, CL, Br and I, preferably F, CL and Br, more preferably F and CL, most preferably F. With reference to carbocyclic aryl and heterocyclic aryl as the "hydrocarbyl" group, by the expression "hydrocarbyl" is meant 2-, 3- or 4-pyridyl, imidazolyl, 2-thiazolyl, 2- or 3-furyl, 2-pyrryl methyl, and 2-thienyl and salts thereof. More preferably, the process of the invention is useful to produce the vinyl and allyl cephem derivatives. More preferably, the process of the invention is especially useful t produce the 3-allyl-, i.e. 3-(2-propenyl)-, 3-cephem, the 3-(3-butenyl)-3-cephem, and the 3-(cis-Z-butenyl)-3-cephem, the 3-(2,3,3-trifluoro-2-propenyl)-3-cephem, the 3-(2-ethoxy-2-propenyl)-3-cephem, and 3-(4-methoxybenzyl)-3-cephem derivates.

The process for producing the 3-hydrocarbyl-3-cephems may employ a phosphine reagent selected from a variety of phosphine compound such as, for example, triphenylphosphine, tri-(3-fluorophenyl)-phosphine tri-(4-chlorophenyl)-phosphine, tri-(3-methoxypheny)-phosphine, diphenylmethylphosphine, dimethylphenylphosphine, tributylphosphine, tri-(2-thienyl)-phosphine, and tri-(2-furyl)-phosphine. Phosphite compounds such as, for example, trimethyl and triethyl and triphenyl and tri-isopropyl phosphites may be substituted for the above-mentioned phosphine compounds. Also, chelating phosphines such as, for example, bis-diphenylphosphinoethane and bis-diphenylphosphinopropane may be substituted for the above phosphines. However, in order to achieve the greatest advantages according to this invention, the phosphine is most preferably tri-(2-furyl)-phosphine.

Although any Pd compound may be used in the process of this invention, preferably the Pd compound is selected from a Pd° compound such as bis(dibenzylideneacetonyl)palladium [Pd(dba)$_2$] and a Pd$^{II}$ compound such as Pd(OAc)$_2$, and PdCl$_2$. The first-named Pd reagent [Pd(dba)$_2$] is especially advantageous in the process according to this invention.

The final product may be isolated and recovered by techniques that are conventional in the field of cephalosporin chemistry such as by column chromatography on a silica gel column or by flash chromatography on SiO$_2$ and characterized by elemental anaylysis, $^1$H-NMR and mass spectroscopy.

The following table (Table I) illustrates but a few representative 3-allyl-, 3-butenyl-, and 3-carbocyclic arylmethyl tributylstannanes, resulting products from reaction with the 3-chloromethyl-3-cephem, III, illustrated above, reaction time and yield (%) of product according to the process of this invention.

The following examples illustrate but a few representative procedures for carrying-out the process according to this invention and are not to be construed as limiting the invention in scope. Example A shows the preparation of a representative starting material. All parts and percentages are by weight and temperatures are in degrees Celsius unless otherwise indicated.

In view of the results obtained as illustrated in the examples, the time and temperature of the reaction in step (B) of the process according to this invention are not believed to be critical and may range from about 20° C. to about 75° C. for about 1 h to about 75 h, preferably about 25°-70° C. for about 1-72 h, depending on the selection and reactivity of the particular reactants and catalyst system. Also, step (B) generally is carried-out in an inert atmosphere such as, for example, under an Argon atmosphere.

TABLE I

Coupling of stannanes$^{(a)}$ with 3-chloromethylcephem I.

| Example | Stannane | Product | Reaction Time | % Yield |
|---|---|---|---|---|
| 1 | CH$_2$=CH-CH$_2$-SnBu$_3$ | 4 | 3 h | 82 |
| 2 | CH$_2$=CH-CH$_2$-CH$_2$-SnBu$_3$ (cis) | 5 | 16 h | 78 |
| 3 | (CH$_3$)$_2$C=CH-SnBu$_3$ | 6 | 72 h | 60 |
| 4 | F$_2$C=CF-SnBu$_3$ | 7 | 72 h | 65 |
| 5 | CH$_2$=C(OEt)-SnBu$_3$ | 8 | 2 h | 71 |

TABLE I-continued
Coupling of stannanes[a] with 3-chloromethylcephem I.

| Example | Stannane | Product | Reaction Time | % Yield |
|---|---|---|---|---|
| 6 | MeO—C$_6$H$_4$—SnBu$_3$ | 9 (cephem with -CH$_2$-C$_6$H$_4$-OMe substituent) | 24 h | 81 |
| 7 | CH$_2$=CH-CH$_2$-SnBu$_3$ | 10 and 11 (allyl-substituted cephems) | 16 h | 57 |

[a] All experiments were carried out in dry THF under Argon with 2% mole Pd(dba)$_2$ and 4% mole tri-(2-furyl)-phosphine at 65° C.
[b] Ratio 10/11 was ca. 5:1 ($^1$H—NMR). R$_1$, R$_2$: see Eq. 1.

EXAMPLE A

Diphenylmethyl 7-[D-2-t-Butoxycarbonylamino-(4-hydroxyphenyl)acetamido]-3-chloromethyl-3-cephem-4-carboxylate

A. Mixed Anhydride

A solution of 10.26 g (0.0384 mole) of D(—)-N-t-butoxycarbonyl-2-(4-hydroxyphenyl)glycine in 150 mL of tetrahydrofuran was cooled to —25° C. in dry-ice-acetone bath. Isobutyl chloroformate (5.37 g, 0.0393 mole) was added followed by 3.94 g (0.0390 mole) of n-methyl morpholine and mixture stirred at —25° C. for 30 min. A precipitate of n-methyl morpholine hydrochloride separated immediately.

B. Coupling

Diphenylmethyl 7-amino-3-chloromethyl-3-cephem-4-carboxylate (14.5 g, 0.0349 mole) suspended in 200 mL tetrahydrofuran was added to the mixed anhydride solution at —25° C. The cooling bath was removed and the mixture was stirred for 2 hrs. The tetrahydrofuran was removed at reduced pressure and the residue dissolved in ethyl acetate. The organic solution was washed once with water, once with 0.5 N hydrochloric acid, twice with dilute sodium bicarbonate and finally twice with water. The solvent was then removed at reduced pressure. The residue was dissolved in 50 mL ethyl acetate and hexane (40 mL) was added to this solution causing material to crystallize. After crystallization was complete, the product was filtered, washed with cold 4:1 hexane-ethyl acetate and dried in vacuo over phosphorus pentoxide yielding 17.86 g (77%) of diphenylmethyl 7-[D-2-t-butoxycarbonyl-amino-(4-hydroxyphenyl)acetamido]-3-chloromethyl-3-cephem-4-carboxylate. The nuclear magnetic resonance spectrum was consistent for the desired product.

EXAMPLE 1

Diphenylmethyl 7-[D-2-t-butoxycarbonylamino-(4-hydroxyphenyl)acetamido]-3-(2-propenyl)-3-cephem-4-carboxylate

Coupling

A mixture of 5.0 g (0.00753 mole) of diphenylmethyl 7-[D-2-t-butoxycarbonylamino-(4-hydroxyphenyl)acetamido]-3-chloromethyl-3-cephem-4-carboxylate, 2.86 g (0.0090 mole) of vinyl tri-n-butyl stannane and 0.070 g (0.0003 mole) of tri(2-furyl)phosphine in 40 mL of tetrahydrofuran (dry), under a Argon atmosphere, was degassed for 30 seconds. Then 0.086 g (0.00015 mole) of palladium(0) bis(dibenzylidene acetone) was added all at once. The reaction mixture was stirred at 70° C. for 5.5 hrs. The solvent was removed at reduced pressure and the residue taken up in acetonitrile. The organic solution was washed twice with n-pentane and the solvent removed at reduced pressure. The residue was chromatographed on 200 g of silica gel yielding 4.24 g (82%) of diphenylmethyl 7-[D-2-t-butoxycarbonyl-amino-(4-hydroxyphenyl)acetamido]-3-(2-propenyl)-3-cephem-4- carboxylate. The nuclear magnetic resonance spectrum was consistent for the desired structure.

Anal. Calcd. for $C_{36}H_{37}N_3O_7S$: C, 65.93; H, 5.69; N, 6.41; S, 4.89. Found: C, 65.89; H, 5.75; N. 6.15; S, 4.66.

Hydrolvsis to carboxylic acid.

7-[D-2-Amino-(4-hydroxyphenyl)acetamido]-3-(2-propenyl)-3-cephem-4-carboxylic acid To 0.75 g of diphenylmethyl 7-[D-2-t-butoxycarbonylamino-(4-hydroxyphenyl)acetamido]-3-(2-propenyl)-3-cephem-4-carboxylate was added 2 mL of anisole followed by 10 mL of trifluoroacetic acid. The reaction mixture was stirred at 4° C. for 40 min. The trifluoroacetic acid was removed at reduced pressure and the residue treated with anhydrous diethyl ether producing a filterable solid. The trifluoroacetate salt of the product was filtered off, washed well with anhydrous diethyl ether and dried in vacuo, over phosphorus pentoxide to give 0.38 g of the material. The salt was dissolved in 10 mL of water and the pH adjusted to 4.8 with dilute sodium bicarbonate. The crystalline product was collected by filtration, washed with cold water and dried in vacuo, over phosphorus pentoxide to yield 0.29 g (62.2%) of 7-[D-2-amino-(4-hydroxyphenyl)acetamido]-3-(2-propenyl)-3-cephem-4-carboxylic acid. The nuclear magnetic resonance and mass spectra were consistent for the desired product.

Anal. Calcd. for $C_{18}H_{19}N_3O_5S \cdot 2H_2O$: C, 50.81; H, 5.45; N. 9.88; S, 7.54 Found: C, 50.39; H, 5.12; N, 9.66; S, 7.40.

EXAMPLE 2

Diphenylmethyl 7-[D-2-t-butoxycarbonylamino-(4-hydroxyphenyl)acetamido]-3-(cis-2-butenyl)-3-cephem-4-carboxylate Coupling A mixture of 1.0 g (0.0015 mole) of diphenylmethyl 7-[D-2-t-butoxycarbonylamino-4-hydroxyphenyl)acetamido]-3-chloromethyl-3-cephem-4-carboxylate, 0.595 g (0.0018 mole) of cis 1-propenyl tri-n-butyl stannane and 0.0139 g (0.00006 mole) tri-(2-furyl)-phosphine in 10 mL of tetrahydrofuran (dry), under a Argon atmosphere, was degassed at reduced pressure for 30 seconds. Then 0.0172 g (0.00003 mole) of palladium(0) bis(dibenzylidene acetone) was added all at once. The reaction mix was stirred at 70° C. for 19 hrs. The solvent was removed at reduced pressure and the residue was chromatographed on 40 g of silica gel yielding 0.79 g (78.6%) of diphenylmethyl 7-[D-2-t-butoxycarbonylamino-(4-hydroxyphenyl)acetamido]-3-(cis-2-butenyl)-3-cephem-4-carboxylate. The nuclear magnetic resonance spectrum was consistent for the desired structure.

Calcd. for $C_{37}H_{39}N_3O_7S$: C, 66.35; H, 5.87; N, 6.23 Found: C, 65.14, 65.21; H, 5.85, 5.80; N, 6.07, 6.07.

Hydrolysis to carboxylic acid

7-[D-2-Amino-(4-hydroxyphenyl)acetamido]-3-(cis-2-butenyl)-3-cephem-4-carboxylic acid To 0.3 g of diphenylmethyl 7-[D-2-t-butoxycarbonylamino-(4-hydroxyphenyl)acetamido]-3-(cis 2-butenyl)-3-cephem-4-carboxylate was added 0.2 mL of anisole followed by 1.5 mL of trifluoroacetic acid. The solution was stirred at 4° C. for 40 min. The solvent was removed at reduced pressure and the residue treated with anhydrous diethyl ether precipitating the trifluoroacetic acid salt. The salt was filtered off, washed well with anhydrous diethyl ether and dired in vacuo over phosphorus pentoxide yielding 0.173 g of the material. The trifluoroacetic acid salt was dissolved in 2 mL of water and the pH of the solution adjusted to 4.25 with dilute sodium bicarbonate. The product crystallized. The solid was filtered off, washed sparingly with cold water and dried in vacuo over phosphorus pentoxide to yield 0.1025 g (56.7%) of 7-[D-2-amino-(4-hydroxyphenyl)-acetamido]-3-(cis-2-butenyl)-3-cephem-4-carboxylic acid. The nuclear magnetic resonance and mass spectra were consistent for the desired structure.

Anal. Calcd. for $C_{19}H_{21}N_3O_5 \cdot H_2O$: C, 55.33; H, 5.38; N, 10.19. Found: C, 55.52; H, 5.42; N, 9.91.

EXAMPLE 4

Diphenylmethyl 7-[D-2-t-butoxycarbonylamino-(4-hydroxyphenyl)acetamido]-3-(2,3,3-trifluoro-2-propenyl)-3-cephem-4-carboxylate Coupling A mixture of 1.25 g (0.00189 mole) of diphenylmethyl 7-[D-2-t-butoxycarbonylamino-(4-hydroxyphenyl)acetamido]-3-chloromethyl-3-cephem-4-carboxylate, 1.04 g (0.0028 mole) of 1,1,2-trifluorovinyl tri-n-butylstannane and 0.0222 g (0.0000947 mole) of tri-(2-furyl)-phosphine in 30 mL of tetrahydrofuran (dry), under atmosphere, was degassed at reduced pressure for 30 seconds. Then 0.027 g (0.0000469 mole) of palladium(0) bis(dibenzylidene acetone) was added all at once. The reaction mix was stirred at 70° C. for 72 hrs. The solvent was removed at reduced pressure and the residue taken up in acetonitrile. The organic solution was washed three times with n-pentane and the solvent removed at reduced pressure. The residue was chromatographed on 40 g of silica gel yielding 0.87 g (64.8%) of diphenylmethyl 7-[D-2-t-butoxycarbonylamino-(4-hydroxyphenyl)acetamido]-3-(2,3,3-trifluoro-2-propenyl)-3-cephem-4-carboxylate. The nuclear magnetic resonance and mass spectra was consistent for the desired structure.

Anal. Calcd. for $C_{36}H_{34}N_3O_7SF_3$: C, 60.92; H, 4.83; N, 5.92; S, 4.52. Found: C, 60.63; H, 4.87; N, 5.77; S, 4.32.

Hydrolysis to Carboxylic Acid

7-[D-2-Amino-(4-hydroxyphenyl)acetamido]-3-(2,3,3-trifluoro-2-propenyl)-3-cephem-4-carboxylic acid To 0.076 g of diphenylmethyl 7-[D-2-t-butoxycarbonylamino-(4-hydroxyphenyl)acetamido]3-(2,3,3-trifluoro-2-propenyl)-3-cephem-4-carboxylate was added 1.0 mL of anisole followed by 5.0 mL of trifluoroacetic acid. The solution was stirred at 4° C. for 40 min. The solvent was removed at reduced pressure and the residue treated with anhydrous diethyl ether precipitating the trifluoroacetic acid salt. The salt was filtered off, washed well with anhydrous diethyl ether and dried in vacuo over phosphorus pentoxide yielding 0.5 g of the material. The trifluoroacetate salt was dissolved in 3 mL of water and the pH of the mixture adjusted to 4.93 with dilute sodium bicarbonate. The product crystallized. The solid was removed by filtration, washed sparingly with cold water and dried in vacuo over phosphorus pentoxide to yield 0.393 g (82.8%) of 7-[D-2-amino-(4-hydroxyphenyl)acetamido]-3-(2,3,3-trifluoro-2-propenyl)-3-cephem-4-carboxylic acid. The nuclear magnetic resonance and mass spectra were consistent for the desired structure.

Anal. Calcd. for $C_{18}H_{16}N_3O_5SF_3H_2O$: C, 46.86; H, 3.93; N, 9.11. Found: C, 46.70; H, 3.96; N, 8.81.

EXAMPLE 5

Diphenylmethyl 7-[D-2-t-butoxycarbonylamino-(4-hydroxyphenyl)acetamido]-3-(2-ethoxy-2-propenyl)-3-cephem-4-carboxylate A mixture of 1.07 g (0.00161 mole) of diphenylmethyl 7-[D-2-t-butoxycarbonylamino-(4-hydroxyphenyl)acetamido]-3-chloromethyl-3-cephem-4-carboxylate, 0.70 g (0.00194 mole) of (1-ethoxyvinyl)-tri-n-butylstannane and 0.015 g (0.00006 mole) of tri(2-furyl)phosphine in 10 mL of tetrahydrofuran (dry), under a Argon atmosphere, was degassed at reduced pressure for 30 seconds. Then 0.018 g (0.00003 mole) of palladium(0) bis(dibenzylidene acetone) was added all at once. The reaction mix was stirred at 70° C. for 2 hrs. The solvent was removed at reduced pressure and the residue taken up in acetonitrile. The organic solution was washed twice with n-pentane and the solvent removed at reduced pressure. The residue was chromatographed on 35 g of silica gel yielding 0.59 g (52.4%) of diphenylmethyl 7-[D-2-t-butoxycarbonylamino-(4-hydroxyphenyl)acetamido]-3-(2-ethoxy-2-propenyl)-3-cephem-4-carboxylate. The nuclear magnetic resonance spectrum was consistent for the desired structure.

Anal. Calcd. for $C_{38}H_{41}N_3O_8S$: C, 65.22; H, 5.91; N, 6.00. Found: C, 64.39; H, 5.36; N, 5.93.

EXAMPLE 7

Diphenylmethyl 7-[D-2-t-butoxycarbonylamino-(4-hydroxyphenyl)acetamido]-3-(3-butenyl)-3-cephem-4-carboxylate Coupling A mixture of 1.0 g (0.0015 mole) of diphenylmethyl 7-[D-2-t-butoxycarbonylamino-(4-hydroxyphenyl)acetamido]-3-chloromethyl-3-cephem-4-carboxylate, 0.745 g (0.00225 mole) allyltri-n-butylstannane and 0.0139 g (0.00006 mole) tri(2-furyl)-phosphine in 10 mL of tetrahydrofuran (dry), under a Argon atmosphere, was degassed at reduced pressure for 30 second. Then 0.0172 g (0.00003 mole) of palladium(0) bis(dibenzylidene acetone) was added all at once. The reaction mix was stirred at 70° C. for 19 hrs. The solvent was removed at reduced pressure and the residue taken up in acetonitrile. The organic solution was washed twice with n-pentane and the solvent again removed at reduced pressure. The residue was chromatographed on 100 g of silica gel yielding 0.44 g of a yellowish white solid. This solid was shown to be a mixture of the product and diphenylmethyl 7-[D-2-t-butoxycarbonylamino-(4-hydroxyphenyl)acetamido]-3-exomethylene-4-(2-propenyl)-4-carboxylate in about a ¼ ratio.

A 0.100 g sample of the mixture was refluxed in 25 mL of toluene for 19 hrs. The solvent was removed at reduced pressure. The residue after chromatography yielded 0.0798 g of diphenylmethyl 7-[D-2-t-butoxycarbonylamino-(4-hydroxyphenyl)acetamido]-3-(3-butenyl)-3-cephem-4-carboxylate. The nuclear magnetic rssonance spectrum was consistent for the desired structure.

Hydrolysis to Carboxylic Acid

7-[D-2-Amino-(4-hydroxyphenyl)acetamido]-3-(3-butenyl)-3-cephem-4-carboxylic acid To 0.0798 g of diphenylmethyl 7-[D-2-t-butoxycarbonylamino(4-hydroxyphenyl)acetamido]-3-(3-butenyl)-3-cephem-4-carboxylate was added 0.1 mL of anisole followed by 0.5 mL of trifluoroacetic acid. The resulting solution was stirred at 4° C. for 40 min. The solvent was then removed at reduced pressure and the residue treated with anhydrous diethyl ether precipitating the trifluoroacetic acid salt. The salt was collected by filtration, washed well with anhydrous diethyl ether and dried in vacuo over phosphorus pentoxide yielding 0584 g of the material. The trifluoroacetate salt was dissolved in 1 mL of water and the pH of the solution adjusted to 5.7 with dilute sodium bicarbonate. The product crystallized. The solid was filtered off, washed sparingly with cold water and dried in vacuo over phosphorus pentoxide to yield 0.0279 g (51.3) of 7-[D-2-amino(4-hydroxyphenyl)acetamido]-3-(3-butenyl)-3-cephem-4-carboxylic acid. The nuclear resonance spectrum was consistent for desired structure.

Anal. Calcd. for $C_{19}H_{21}N_3O_5S$ $3H_2O$: C, 49.88; H, 5.95; N, 9.18. Found: C, 49.93; H, 6.02; N. 8.81.

EXAMPLE 8

7-[D-2-Amino-(4-hydroxyphenyl)acetamido]-3-(2-oxapropyl)-3-3-cephem-4-carboxylic acid.

To 0.57 g of diphenylmethyl 7-[D-2-t-butoxycarbonylamino(4-hydroxyphenyl)acetamido]-3-(2-ethoxy-2-propenyl)-3-cephem-4-carboxylate was added 1.6 mL of anisole followed by 8.0 mL of trifluoroacetic acid. The solution was stirred at 4° C. for 40 min. The reaction mix was diluted with 30–50 mL of anhydrous diethyl ether causing the trifluoroacetic acid salt to precipitate. The salt was filtered off, washed well with anhydrous diethyl ether and dried in vacuo over phosphorus pentoxide yielding 0.33 g of the material. The salt was dissolved in 2 mL of water and the pH of the solution adjusted to 4.3 with dilute sodium bicarbonate. Upon addition of 2 mL of acetone to the aqueous solution, the product crystallized. The solid was collected by filtration, washed sparingly with acetone and dried in vacuo over phosphorus pentoxide to yield 0.080 g (24.2%) of 7-[D-2-amino-(4-hydroxyphenyl)acetamido]-3-(2-oxa-propyl)-3-cephem-4-carboxylic acid. The nuclear magnetic spectrum was consistent for the desired structure.

Anal. Calcd. for $C_{18}H_{19}N_3O_6S$ $0.5$ $H_2O$: C, 52.16; H, 4.87; N, 10.14. Found: C, 51.81; H, 4.75; N, 9.74.

EXAMPLE 9

Diphenylmethyl 7-[D-2-t-butoxycarbonylamino-(4-hydroxyphenyl)acetamido]-3-exomethylene-4-(2-propenyl)-4-carboxylate.

Coupling

A mixture of 1.0 g (0.00151 mole) of diphenylmethyl 7-[D-2-t-butoxycarbonylamino-(4-hydroxyphenyl)acetamido]-3-chloromethyl-3-cephem-4-carboxylate, 0.745 g (0.00225 mole) allyl tri-n-butylstannane and 0.0139 g (0.00006 mole) tri(2-furyl)phosphine in 10 mL of tetrahydrofuran (dry), under a Argon atmosphere, was degassed at reduced pressure for 30 seconds. Then 0.0172 g (0.00003 mole) of palladium(0) bis(dibenzylidene acetone) was added all at once. The reaction mix was stirred at 70° C. for 19 hrs. The solvent was removed at reduced pressure and the residue taken up in acetonitrile. The organic solution was washed twice with n-pentane and the solvent again removed at reduced pressure. The residue was chromatographed on 100 g of silica gel yielding 0.44 g of diphenylmethyl 7-[D-2-t-butoxycarbonylamino-(4-hydroxyphenyl)acetamido]-3-exomethylene-4-(2-propenyl)-4-carboxylate. The nuclear magnetic resonance spectrum was consistent for the desired structure.

Hydrolysis to Carboxylic Acid

7-[D-2-amino-(4-hydroxyphenyl)acetamido]-3-exomethylene-3-cephem-4-(2-propenyl)-4-carboxylic acid-trifluoroacetic acid salt.

To 0.077 g of diphenylmethyl 7-[D-2-t-butoxycarbonylamino(4-hydroxyphenyl)acetamido]-3-exomethylene-3-cephem-4-(2-propenyl)-4-carboxylate was added 0.95 mL of anisole followed by 4.5 mL of trifluoroacetic acid. The reaction mixture was stirred at 4° C. for 40 min. The 4 mL of anhydrous diethyl ether was added producing a solid. The material was filtered off, washed well with anhydrous diethyl ether yielding 0.196 g (34.1%) of 7-[D-2-amino-(4-hydroxyphenyl)acetamido]-3-exomethylene-3-cephem-4-(2-propenyl)-4-carboxylic acid trifluoroacetic acid salt. The nuclear resonance and magnetic resonance and mass spectra were consistent for the desired structure.

Anal. Calcd. for $C_{19}H_{21}N_3O_5S \cdot CF_3CO_2H$: C, 48.74; H, 4.29; N, 8.12. Found: C, 49.65; H, 4.37; N, 7.71.

EXAMPLE 10

Benzhydryl 7-amino-3-allyl-3-cephem-4-carboxylate

To a solution of benzhydryl 7-benzylidineamino-3-chloromethyl-3-cephem-4-carboxylate (3.00 g.,5.92 mmol) in dry THF (50 mL), vinyltributyltin (Aldrich, 2.25 g., 7.0 mmol) was added as a THF (5mL) solution, followed by tri-(2-furyl)phosphine (0.055 g., 0.235 mmol) and palladium (0) bis (dibenzylideneacetone) [Pd(dba)$_2$](Aldrich, 0.068 g., 0.117 mmol). The purple solution slowly turned yellow (indicating formation of a palladium-phosphine complex). The reaction mixture was refluxed for 4–5h under Argon. HPLC (C-18,55% acetonitrile in pH 6.5 buffer) was used to monitor the reaction. TLC (SiO$_3$ Ethyl acetate in Hexane) is also suitable but less accurate. Completion was also signaled by a rather sudden darkening of the solution (from yellow to reddish-brown), presumably due to the fact that the palladium complex decomposes once its catalytic cycle is complete. The first intermediate product, benzhydryl 7-benzylidineamino-3-allyl-3-cephem-4-carboxylate was isolated by evaporation of the solvent, after washing out the tin by-products with pentane (3×75 mL) from a solution of the first intermediate product in Acetonitrile (100 mL). The first intermediate product could be purified, if desired, by flash chromatography (SiO$_2$, 30% Ethyl acetate in hexane), with some losses due to Schiff base hydrolysis, to yield a tan solid.

NMR: (CDCl$_3$, 360 MHz) δ 8.60 (1H,d,J=1.5 Hz) 7.8 (2H,dd, J=8.1 Hz,J'=1.5 Hz) 7.5–7.2 (13H,m) 6.93 (1H,s) 5.76 (1H,m) 5.4 (1H,dd, J=5.1 Hz,J'=1.5 Hz) 5.33 (1H,m) 5.19 (1H,d,J=5.1 Hz) 5.08 (1H,m) 3.50 (1H,d,J=18 Hz) 3.33 (1H,d,J=18 Hz) 3.32 (1H,m) 2.87 (1H,dd,J$_{gem}$=14 Hz,J$_{vic}$=7.5 Hz).

The crude first intermediate could be directly hydrolyzed as follows: Methanol (100 mL) was added to it, followed by conc. HCl (10 mL) slowly; after stirring for 30 min at room temperature and neutralizing with NaHC0$_3$, the product was extracted with ethyl acetate out of an aqueous solution and flash chromatographed on SiO$_2$ with 60% Ethyl acetate in hexane, to yield second intermediate product, benzhydryl7-amino-3-cephem-4-carboxylate, as a tan solid. (1.238 g., 51.5% overall).

NMR: (CDCl$_3$, 360 MHz) δ 7.3–7.1 (10H,m) 6.97 (1H,s) 5.75 (1H,s) 5.05 (1H,dd, J$_{cis}$=9 Hz,J$_{1r}$=1.5Hz) 5.02 (1H,dd, J$_{trans}$=17.5 Hz,J$_{1r}$=1.5 Hz) 4.92 (1H,d,J=4.8 Hz) 4.78 (1H,d,J=4.8 Hz) 3.42 (1H, d,J=18 Hz) 3.28 (1H,ddt, J$_{gem}$=14 Hz, J$_{vic}$=5.2 Hz, J$_{1r}$=1.5Hz) 3.25 (1H,d,J=18 Hz) 2.83 (1H,dd,J$_{gem}$=14 Hz, J$_{vic}$=7.5 Hz) 1.75 (2H, br s., exchangeable).

7-Amino-3-Allyl-3-cephem-4-carboxylic acid

Benzhydryl 7-benzylideneamino-3-allyl-3-cephem-4-carboxylate (2.00 g., 4.0 mmol) produced as described above was added portionwise to a mixture of formic acid (8 mL) and conc. HCl (0.65 mL). The mixture was stirred at room temperature for 2 h, the excess formic acid was evaporated in vacuo, and water (15 mL) and conc. HCl (1.2 mL) were added to the residue. The resulting solution was washed with dichloromethane (2×6 mL), cooled to 0°–5° C., and the pH adjusted to 2.8 with 6N NaOH. The resulting slurry was stirred at 0° C for 39 min. The final product (0.77–0.88 g., 79–86%) was isolated by filtration, washing with ice-cold water (2×4 mL) and drying at 40° C. for 15 h in vacuo.

NMR: (D$_2$O / DCl, 360 MHz) δ 5.88 (1H,m) 5.32 (1H,d, J=4. 8 Hz) 5.22–5.00 (3H,m) 3.6 (2H,m) 3.45 (1H,dd,J$_{gem}$=14 Hz,J$_{vic}$=6 Hz) 3.27 (1H,dd. J$_{gem}$=14Hz,J$_{vic}$=6.8 Hz).

Anal. Calcd. for $C_{10}H_{12}N_2O_3S$: C, 49.48; H, 5.04; Found (corr.): C,48,56; H, 5.12; N, 11.50; S, 13.61. %H$_2$O: 0.65 (K.F.)

Additional examples of 3-allyl-3-cephems which were produced using the process according to this invention are described in Table II which follows.

TABLE II

Additional Examples of Palladiuim-Catalyzed Coupling of 3-Chloromethyl-3-Cephems with Stannanes

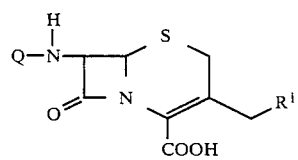

| Ex. No. | Stannane | Product |
| --- | --- | --- |
| 11 | ⟶\SnBu$_3$ | Q = 7-[Z—(2-aminothiazol-4-yl)-2-methoxyiminoacetamido]-3-allyl-3-cephem-4-carboxylic acid |
| 12 | ⟶\SnBu$_3$ | Q = 7-[Z—(2-aminothiazol-4-yl)-2-methoxyiminoacetamido]-3-allyl-3-cephem-4-carboxylic acid (Pivaloyloxymethyl ester of Ex. 11) |

TABLE II-continued

Additional Examples of Palladiuim-Catalyzed Coupling of
3-Chloromethyl-3-Cephems with Stannanes

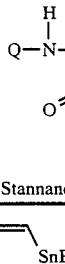

| Ex. No. | Stannane | Product |
| --- | --- | --- |
| 13 | SnBu$_3$ | Q = 7-[Z—(2-aminothiazol-4-yl)-2-methoxyiminoacetamido]-3-allyl-3-cephem-4-carboxylic acid (Acetoxyethyl ester of Ex. 11) |
| 14 | SnBu$_3$ | Q = 7-[(Z)—2-(2-aminothiazol-4-yl)-2-hydroxyiminoacetamido]-3-allyl-3-cephem-4-carboxylic acid |
| 15 | SnBu$_3$ | Q = 7-[(Z)—2-(2-aminothiazol-4-yl)-2-hydroxyiminoacetamido]-3-allyl-3-cephem-4-carboxylic acid (Pivaloyloxymethyl ester of Ex. 14) |
| 16 | SnBu$_3$ | Q = 7-[(Z)—2-(2-aminothiazol-4-yl)-2-hydroxyiminoacetamido]-3-allyl-3-cephem-4-carboxylic acid (Acetoxyethyl ester of Ex. 14) |

The compounds of Formula III produced according to the process of this invention may be provided as pharmaceutically acceptable acid addition and base salts wherein the anion or cation, respectively, does not contribute significantly to the toxicity of the salt and which salts are compatible with the standard and conventional pharmaceutically acceptable carriers and other conventional adjuvants and excipients customarily employed in producing pharmaceutical compositions adapted for oral or parenteral administration. The acid addition salts are formed by conventional techniques involving reaction for compounds of Formula III with mineral acids such as, for example, hydrochloric acid, hydrobromic acid, phosphoric acid, and sulfuric acid, and with organic carboxylic and sulfonic, acids such as, for example, acetic acid, citric acid, maleic acid, succinic acid, benzoic acid, tartaric acid, ascorbic acid, methane sulfonic acid, ethanesulfonic acid, p-toluenesulfonic acid, and the like.

Pharmaceutically acceptable base salts are formed by conventional techniques involving reaction of the compounds of Formula III with alkali (Na,K) and alkaline earth (Ba, Zn, Mg) metal bases, more preferably with alkali metal bases such as, for example, dilute solutions of sodium hydroxide, potassium carbonate, and sodium bicarbonate. Also, pharmaceutically acceptable base salts are formed by conventional techniques involving reaction with amines such as, for example, triethylamine, dibenzylamine, N,N'-dibenzylethylenediamine, procaine and equivalent amines.

Pharmaceutically acceptable esters include those esters which are active per se or which function as pro-drugs by being hydrolyzed in the body to yield the active antibiotic per se. Suitable esters of the latter type include the phenacyl, acetoxymethyl, pivaloyloxymethyl, α-acetoxybenzyl, 3-phthalidyl, 5-indanyl, methoxymethyl, benzoyloxymethyl, glycyoxymethyl, and other esters known in the cephalosporin and penicillin arts.

The pharmaceutical compositions of compounds produced according to the process of this invention may be prepared by combining the compounds of this invention with a solid or liquid pharmaceutically acceptable carrier and, optionally, with pharmaceutically acceptable adjuvants and excipients employing standard and conventional techniques. Solid form compositions include powders, tablets, dispersible granules, capsules, cachets and suppositories. A solid carrier can be at least one substance which may also function as a diluent, flavoring agent, solubilizer, lubricant, suspending agent, binder, tablet disintegrating agent, and encapsulating agent. Inert solid carriers include magnesium carbonate, magnesium stearate, talc, sugar, lactose, pectin, dextrin, starch, gelatin, cellulosic materials, low melting wax, cocoa butter, and the like. Liquid form compositions include solutions, suspensions and emulsions. For example, there may be provided solutions of the compounds of this invention dissolved in water and water-propylene glycol and water-polyethylene glycol systems, optionally containing suitable conventional coloring agents, flavoring agents, stabilizers and thickening agents.

Preferably, the pharmaceutical composition is provided employing conventional techniques in unit dosage form containing appropriate amounts of the active component, that is, the compound of Formula I according to this invention.

The quantity of active component, that is the compound of Formula III according to this invention, in the pharmaceutical composition and unit dosage form thereof may be varied or adjusted widely depending upon the particular application, the potency of the particular compound, and the desired concentration. Generally, the quantity of active component will range between 0.5% to about 90% by weight of the composition.

In therapeutic use for treating, or combatting Gram-positive and Gram-negative bacterial infections in warm-blooded animals, the compounds will be administered at a dosage to obtain and maintain a concentration that is, an amount, or blood-level in the animal undergoing treatment which will be antibacterially effective. Generally, such antibacterially effective amount of dosage will be in the range of from about 100 mg to about 5000 mg per day. It is to be understood that the dosages may vary depending upon the requirement of the patient, the severity of the bacterial infection being treated, and the particular compound being used. Also, it is to be understood that the initial dosage administered may be increased beyond the above upper level in order to rapidly achieve the desired blood-level or the initial dosage may be smaller than the optimum and the daily dosage may be progressively increased during the course of treatment depending on the particular situation.

The compounds of formula III produced according to the process of this invention are advantageously administered parenterally, i.e. by injection, for example, by intravenous injection or by other parenteral routes of administration. Pharmaceutical compositions for parenteral administration will generally contain a pharmaceutically acceptable amount of the compound according to formula I as a soluble salt (acid addition salt or base salt) dissolved in a pharmaceutically acceptable liquid carrier such as, for example, water for injection and a buffer to provide a suitably buffered isotonic solution having a pH of about 3.5-7. Suitable buffering agents include, for example, trisodium orthophosphate, sodium bicarbonate, sodium citrate, N-methylglucamine, L(+)-lysine and L(+)-arginine to name but a few representative buffering agents. The compound according to formula I generally will be dissolved in the carrier in an amount sufficient to provide a pharmaceutically acceptable injectable concentration in the range of about 1 mg/ml to about 400mg/ml of solution. The resulting liquid pharmaceutical composition will be administered so as to obtain the above-mentioned antibacterially effective amount of dosage in the range of from about 100 mg to about 5000 mg per day.

The following table (Table III) illustrates the activity of several representative compounds produced by the process according to this invention.

TABLE III

| ORGANISM | Antibacterial Activity MIC (g/ml) | |
|---|---|---|
| | Ex. 1 | Ex. 2 |
| S. pneumoniae | 0.06 | 0.06 |
| S. pyogenes | 0.03 | 0.008 |
| S. faecalis | 16 | 4 |
| S. aureus | 0.03 | 0.06 |
| S. aureus/+50% serum | 0.25 | 0.25 |
| S. aureus/Pen. Res. | 1 | 32 |
| S. aureus/Meth. Res. | >16 | >125 |
| E. coli | 2 | 32 |
| E. coli | 8 | 32 |
| K. pneumoniae | 2 | 8 |
| K. pneumoniae | >16 | >125 |
| E. cloacae | >16 | >125 |

What is claimed is:

1. A process for producing a cephalosporin compound having the ceph-3-em nucleus bearing known cephalosporin antibiotic substituents at the 4, 7 and 8 positions, and the —CH$_2$R$^1$ substituent at the 3-position wherein R$^1$ is selected from the group consisting of vinyl, substituted vinyl, phenyl, substituted phenyl, 2-, 3-, or 4-pyridyl, imidazolyl, 2-thiazolyl, 2-, or 3-furyl, and 2-thienyl wherein said substituents relative to substituted vinyl and substituted phenyl are selected from alkyl and alkoxy each having 1 to 4 carbon atoms, fluorine, chlorine, bromine, and iodine which comprises contacting in a polar aprotic solvent of a 3-halomethyl-ceph-3-em compound having substituents at the 4, 7, and 8 positions which are non-reactive under the reaction conditions with the reagents employed, and
    (a) at least an equimolar amount of R$^1$-trialklstannane wherein said alkyl has 1-4 carbon atoms, and R$^1$ has the same definition given above:
    (b) 1–10 mole percent of a Pd$^0$ or PD$^{II}$ compound: and
    (c) 3–30 mole percent of a phosphine reagent selected from tri(2-furyl)phosphine and tri(2-thienyl)phosphine at a temperature of about 20°–75° C. for from about 1 to 72 hours.

2. The process of claim 1 wherein said polar aprotic solvent is selected from the group consisting of 1-methyl-2-pyrrolidone, tetrahydrofuran, acetonitrile, dimethylsulfoxide, dimethylformamide, ethylene glycol dimethyl ether, dioxane, hexamethylphosphoric amide, acetone, nitromethane, and nitrobenzene.

3. The process of claim 1 wherein said polar aprotic solvent is tetrahydrofuran.

4. A process according to claim 1 wherein the phosphine is tri-(2-furyl)-phosphine.

5. A process according to claim 1 wherein the group, R$^1$, is selected from unsubstituted and substituted vinyl and allyl groups.

6. A process according to claim 1 wherein the group, R$^1$ is selected from vinyl, allyl (2-propenyl), 3-butenyl cis-2-butenyl, trifluorovinyl, ethoxy vinyl and 4-methoxyphenyl groups.

7. A process according to claim 1 wherein the Pd compound is bis(dibenzylidenacetonyl)palladium.

* * * * *